[19] United States Patent
Trotta

[11] Patent Number: 5,190,751
[45] Date of Patent: Mar. 2, 1993

US005190751A

[54] TREATMENT OF CERTAIN LEUKEMIAS WITH A COMBINATION OF GAMMA INTERFERON AND ALPHA INTERFERON

[75] Inventor: Paul P. Trotta, Rutherford, N.J.

[73] Assignee: Schering Corporation, Kenilworth, N.J.

[21] Appl. No.: 766,911

[22] Filed: Sep. 26, 1991

Related U.S. Application Data

[63] Continuation of Ser. No. 4,731, Jan. 20, 1987, abandoned.

[51] Int. Cl.$^5$ .............................................. A61K 37/66
[52] U.S. Cl. .................................. 424/85.4; 530/351; 424/85.5; 424/85.7
[58] Field of Search .............. 530/351; 424/85.4, 85.5, 424/85.7

[56] References Cited

U.S. PATENT DOCUMENTS 4,289,690 9/1981 Pestka et al. ..................... 260/112 R
4,503,035 3/1985 Pestka et al. .......................... 424/85

FOREIGN PATENT DOCUMENTS 88540 9/1983 European Pat. Off. .
107498 5/1984 European Pat. Off. .
0032134 8/1984 European Pat. Off. .
8604067 7/1986 PCT Int'l Appl. .

OTHER PUBLICATIONS

Fleishman et al., Antiviral Research, vol. 4, pp. 357–360, 1984.
Denz et al., J. Interferon Research, vol. 5, pp. 147–157, 1985.
Gray et al., Nature, 295 503–508 (1982).
Epstein, Nature, 295, 453–454 (1982).
Nagata et al., Nature, 284, 316–320 (1980).
Borden et al., Progress in Hematology, vol. XII, Brown, editor, pp. 299–339 (1981).
Gresser et al., Biochim, Biophys, Acta. 516, 231–247 (1978).
Gresser, Chemotherapy-A Comprehensive Treatise, Becher, F. editor vol. 5, pp. 521–571 (1977).
Einhorn et al., Human Interferon Production and Clinical Use, Stinebring et al., editors pp. 159–174 (1977).
Weigent et al., Inf., and Immun. 40 (1) 35–38 (1983).
Fleischmann, Jr. et al., J. Interferon Res. 4, 265–274 (1984).

*Primary Examiner*—Robert J. Hill, Jr.
*Assistant Examiner*—Shelly J. Guest
*Attorney, Agent, or Firm*—Thomas D. Hoffman; Henry C. Jeanette; Matthew Boxer

[57] ABSTRACT

Human leukemia T-cells and B-cells are inhibited from proliferating by treatment with a combination of recombinant human alpha and gamma interferons, either simultaneously or sequentially, and the alpha interferon is preferably recombinant human alfa-2b interferon.

4 Claims, No Drawings

TREATMENT OF CERTAIN LEUKEMIAS WITH A COMBINATION OF GAMMA INTERFERON AND ALPHA INTERFERON

This is a continuation of application Ser. No. 07/004,731 filed Jan. 20, 1987, now abandoned.

BACKGROUND

This invention relates to a method of inhibiting the proliferation of cells of certain susceptible leukemias with combinations of (a) recombinant DNA derived human gamma interferon (hIFN-γ) sometimes referred to as human immune interferon and (b) recombinant DNA derived human alpha interferon, which in combination display greater antiproliferative effects against human leukemia cells than is expected from their individual activities.

Gamma interferon has a number of characteristics known in the art that differentiate it from alpha and beta interferons. Among these differences are antigenic distinctiveness and higher levels of immunoregulatory and antitumor activity. Human gamma interferon may be produced by T-lymphocytes stimulated by mitogens or antigens to which they are sensitized. It may also be obtained through cloning and expression techniques now well known in the art.

Although the source of the human gamma interferon used in this invention is not critical, it is required that such hIFN-γ be of a high purity material that is not contaminated by cell constituents or cell debris of the interferon-expressing cell. A preferred hIFN-γ used in this invention is produced by recombinant DNA technology and then purified as taught in Japanese Patent Application No. 281376, filed Dec. 27, 1984 and foreign counterparts thereof, e.g. PCT International Publication No. 8604067 published Jul. 17. 1986. The purification process comprises adding one or more salts of zinc or copper and polyethyleneimine in the extraction. More particularly, it comprises suspending the culture cells of a recombinant microorganism in a buffer solution containing one or more salts of zinc or copper, e.g. zinc chloride, zinc sulfate, zinc acetate, zinc acetylacetonate and copper sulfate, in a range of about 0.5-5 mM in the case of zinc salts and 0.01-3 mM in the case of copper salts, disrupting the cells, then adding polyethyleneimine to the centrifuged supernatant, e.g. to a final concentration of 0.5-1.1%, and subsequently purifying by a conventional method, e.g. combining several chromatographic methods and dialysis.

Human gamma interferon can be made, for example, by the procedures disclosed in Gray, et al., Nature, 295, 503-508 (1982) and Epstein, Nature, 295, 453-454 (1982).

Human alpha interferon is a naturally occurring mixture of at least eleven compounds including those designated alpha-1 interferon and alpha-2 interferon. Alpha interferon exhibiting biological properties similar to those of naturally occurring human or leukocyte interferon can be made by recombinant methods.

A number of alpha interferon species or components are known and are usually designated by a numeral after the Greek letter alpha, and all are contemplated for use in this invention. Thus, the species designated "human alpha-1 interferon" is contemplated for use in this invention and "human alpha-2 interferon" which under USAN, is designated Interferon Alfa-2b, is also contemplated for use in this invention. "Human interferon alfa-2b" is used herein when referring to human alpha-2 interferon. Interferon alfa-2b is the preferred species of human interferon alfa-2.

Human interferon alfa-2 can be produced in bacteria using recombinant techniques. In addition, human interferon alfa-2b may be prepared by recombinant-DNA methods disclosed by Nagata et al., Nature, 284, 316-320 (1980), European Patent 32,134 and U.S. Pat. No. 4,289,690. Various interferon alfa-2 species are disclosed in U.S. Pat. No. 4,503,035. The preferred human interferon alfa-2b used in this invention is also denoted "hIFN-α2b".

To date, much has been learned about the effect of the interferons on cell proliferation.

Borden et al., Progress in Hematology, Vol XII, Brown, E. B., editor, pp 299-339 (1981) found that interferons inhibit proliferation of normal and transformed cells in vitro.

Gresser et al., Biochim. Biophys. Acta, 516, 231-247 (1978) and Chemotherapy-A Comprehensive Treatise, Becker, F. editor, Vol. 5, pp 521-571 (1977) used murine systems and demonstrated that relatively impure interferon in vitro results in a decreased rate of cell proliferation, lower cell-saturation densities and decreased colony formation in agarose. Inhibitory effects were observed using mouse L929, L1210, Ehrlich ascites, primary embryo and primary weanling kidney cells.

Different types of cells differ in sensitivity to interferons, and cell inhibitory concentrations of interferons can vary widely, i.e. from 10-1000 units, see Borden et al. supra. Among the tumor cells of established cell lines studied in vitro, Einhorn et al., Human Interferon Production and Clinical Use, Stinebring et al., editors, pp 159-174 (1977), found lymphoid leukemias to be sensitive to interferons. The interferons used in these experiments were unpurified materials and it is not clear if the impurities affected the test results.

European Patent Application, Publication No. 0107498, Oct. 24, 1983, discloses combinations of purified human gamma interferon and human alpha interferon made by recombinant methods which exhibit activities higher than could have been fairly predicted based on their respective activities when tested alone. The tests were conducted using the human melanoma cell line Hs294T. However, there is no disclosure that leukemias are susceptible to such treatment.

SUMMARY OF THE INVENTION

This invention relates to inhibiting the proliferation of susceptible leukemia cells with a cell proliferation inhibiting amount of a combination of recombinant human gamma interferon and recombinant human alpha interferon (preferably hIFN-α2b) sufficient to inhibit the proliferation of the cells thereof. When the susceptible leukemia cells are in an animal, including humans, the preferred mode of administration is parenteral, i.e. intravenous, intramuscular, subcutaneous and intraperitoneal, although enteral modes, e.g.; oral, nasal, and the like, as well as topical modes of administration are also contemplated. The interferons can be administered simultaneously or sequentially.

MATERIALS AND METHODS

In order to determine the antiproliferative effects against human T-cell and human B-cell lines, it is possible to run tests on cell cultures using suspension cultures of the cell lines propagated in medium RPMI 1640 supplemented with 10% heat-inactivated fetal bovine serum, 5 μM of 2-mercaptoethanol, 100 units/ml penicillin, 100 μg/ml of streptomycin, and 50 μg/ml of gentamicin as described in Moore, G. E., Human Cells in vitro, Fogh, J. editor, pp 299–331 (1975) and Ohnuma et al., J. Natl. Cancer Inst. 60 1117–20 (1978).

The cell lines used are readily available. The human T-cell lines used were MOLT-3 (ATCC CRL 1552), MOLT-4 (ATTC CRL 1582), HSB-2 (Tumor Institute, University of Alabama at Birmingham, Ala.) and RPMI 8402 (Mount Sinai School of Medicine, New York, N.Y.); the human B-cell lines used were BALM-2 and DND-39A (Mount Sinai School of Medicine, NY, N.Y.), Daudi (ATTC CCL 213) and SB (Tumor Institute, University of Alabama at Birmingham, Ala.).

The above cultures were reseeded at 3- and 4-day intervals at $2.0$–$3.0 \times 10^5$ cells/ml in 75 cm² tissue culture flasks in a total volume of 100 ml per flask. The cell populations exponentially proliferate between cell densities of $2.0 \times 10^5$ to $1.5 \times 10^6$ cells/ml.

Interferons

The hIFN-α2b used in the tests had a specific activity of $1.5 \times 10^8$ International Reference Units (IRU) per mg of protein and the recombinant human gamma interferon had a specific activity of $2 \times 10^6$ IRU/mg of protein.

Experimental Procedure

The cell lines were propagated in RPMI 1640 medium supplemented with 10% heat inactivated fetal bovine serum as described above. The cell cultures were initiated at a cell density of $2.0 \times 10^5$ cells/ml in a total volume of 24 ml in 25 cm² Corning tissue culture flasks and incubated at 37° C. as stationary suspension cultures. The interferons were diluted to designated concentrations in RPMI 1640 medium supplemented with 10% heat inactivated fetal bovine serum. Adriamycin used as a positive control, was dissolved in sterile deionized water and diluted in cell culture medium supplemented with 10% heat inactivated fetal bovine serum to a final concentration of 0.2 μg/ml which is the concentration comparable to drug levels in the tissues of patients and experimental animals during therapy.

In the experiments, 24 hours after the cell cultures were initiated, the proliferating cell populations were exposed to different concentrations of human aloha-2 interferon, preferably, interferon alfa-2b, for 24 and 48 hours, e.g. 0.0066, 0.066, 0.66 and 6.66 μg/ml. At 24 and 48 hours, samples were withdrawn from the samples treated with test drug, untreated control and treated with control drug and counted in a hemacytometer. Viable cell (trypan-blue-excluding cells) counts were used in determining the effect of human alfa-2b interferon and adriamycin on the proliferation of the cultures.

In other experiments, either human alfa-2b interferon or human gamma interferon at various concentrations, e.g. 0.0066, 0.066, 0.66 and 6.66 μg/ml, was added at the time of initiation of cell cultures, and the number of cells monitored as a function of time through 96 hours, i.e. at 24, 48, 72 and 96 hours. At each time interval, samples were withdrawn and counted in a hemacytometer. Interferon assay results are expressed as percent growth inhibition calculated according to the following equation:

$$\text{Percent Growth Inhibition} = 1.0 - \frac{NT_t - NC_o}{NC_t - NC_o} \times 100$$

$NT_t$ = Cell density of treated culture at time $T$.

$NC_t$ = Cell density of control culture at time $T$.

$NC_o$ = The initial cell density of the culture prior to addition of interferon or adriamycin.

The results expressed in % GI (Growth Inhibition) are summarized in Tables I and II.

TABLE 1

Effect of Human alfa-2b. Interferon on Human B- and T-cell Leukemias

| LEUKEMIA CELL TYPE | | CONCENTRATIONS μG/ML, hIFN-α-2b | | | | ADR μG/ML |
|---|---|---|---|---|---|---|
| | | 0.0066 | 0.066 | 0.66 | 6.66 | 0.2 |
| Human B-Cell SB | % GI | 60;47 | 60;47 | 60;47 | 60;47 | 100 |
| | Hours | 24;48 | 24;48 | 24;48 | 24;48 | 24–48 |
| Human B-Cell DND-39A | % GI | 0;19 | 0;19 | 0;42 | 85;42 | 100 |
| | Hours | 24;49 | 24;48 | 24;48 | 24;48 | 24–48 |
| Human B-Cell BALM-2 | % GI | 0;27 | 39;50 | 69;50 | 69;66 | 100 |
| | Hours | 24;48 | 24;48 | 24;48 | 24;48 | 24–48 |
| Human T-Cell MOLT-4 | % GI | 100;86 | 100;86 | 100;86 | 100;86 | 100 |
| | Hours | 24;48 | 24;48 | 24;48 | 24;48 | 24–48 |
| Human T-Cell MOLT-3 | % GI | 62;0 | 62;0 | 62;0 | 62;0 | 100 |
| | Hours | 24;48 | 24;48 | 24;48 | 24;48 | 24–48 |
| Human B-Cell Daudi | % GI | 0 | 0 | 0 | 0 | 100 |
| | Hours | 24;48 | 24;48 | 24;48 | 24;48 | 24–48 |
| Human T-Cell HSB-2 | % GI | 0 | 0 | 0 | 0 | 100 |
| | Hours | 24;48 | 24;48 | 24;48 | 24;48 | 24–48 |
| Hman T-Cell RPMI 8402 | % GI | 0;42 | 0;42 | 0;42 | 0;42 | 100 |
| | Hours | 24;48 | 24;48 | 24;48 | 24;48 | 24–48 |
| Human B-Cell Daudi | % GI | 0;100 | 0;100 | 0;100 | 0;100 | 100;NVC |
| | Hours | 48;72–96 | 48;72–96 | 48;72–96 | 48;72–96 | 48;72–96 |
| Human B-Cell Daudi | % GI | 0 | 0;87;70 | 0;87;100 | 0;87;100 | 100 |
| | Hours | 24;72;96 | 24;72;96 | 24;72;96 | 24;72;96 | 24;72;96 |
| Human T-Cell RPMI 8402 | % GI | 0 | 0;46;25 | 0;46;53 | 0;46;78 | 100 |
| | Hours | 48–96 | 48;27;96 | 48;72;96 | 48;72;96 | 48–96 |
| Human T-Cell MOLT-4 | % GI | 0 | 0 | 0;36;28 | 0;52;44 | 100 |
| | Hours | 24–96 | 24–96 | 24–48;72;96 | 24–48;72;96 | 24–96 |
| Human T-Cell | % GI | 0;26 | 0;26 | 0;26 | 0;55 | 100 |

TABLE I-continued

Effect of Human alfa-2b. Interferon on
Human B- and T-cell Leukemias

| LEUKEMIA CELL TYPE | | CONCENTRATIONS µG/ML, hIFN-α-2b | | | | ADR µG/ML |
|---|---|---|---|---|---|---|
| | | 0.0066 | 0.066 | 0.66 | 6.66 | 0.2 |
| MOLT-3 | Hours | 24–48;72 | 24–48;72 | 24–48;72 | 24–48;72 | 24–72 |

NVC = No viable cells.
GI = Growth Inhibition

TABLE II

Effect of Human Gamma Interferon
on Human B- and T-Cell Leukemias

| LEUKEMIA CELL TYPE | | CONCENTRATIONS NG/ML, hIFN-γ | | | | ADR µG/ML |
|---|---|---|---|---|---|---|
| | | 0.0066 | 0.066 | 0.66 | 6.66 | 0.2 |
| Human B-Cell SB | % GI | 0 | 0 | 0 | 0 | 100 |
| | Hours | 24;48 | 24;48 | 24;48 | 24;48 | 24–48 |
| Human T-Cell MOLT-4 | % GI | 0 | 0 | 0 | 0 | 100 |
| | Hours | 24;48 | 24;48 | 24;48 | 24;48 | 24–48 |
| Human B-Cell DND-39A | % GI | 0;32 | 0;62;32 | 0;62;32 | 0;87;32 | 100 |
| | Hours | 24–48;72 | 24;48;72 | 24;48;72 | 24;48;72 | 24–72 |
| Human T-Cell MOLT-3 | % GI | 100;64;0 | 100;64;0 | 100;64;0 | 100;64;0 | 100 |
| | Hours | 24;48;72 | 24;48;72 | 24;48;72 | 24;48;72 | 24–72 |
| Human B-Cell Daudi | % GI | 0 | 0 | 0 | 0 | 100 |
| | Hours | 48–72 | 48–72 | 48–72 | 48–72 | 48–72 |
| Human T-Cell HSB-2 | % GI | 0 | 0 | 0 | 0 | 100;NVC |
| | Hours | 48–72 | 48–72 | 48–72 | 48–72 | 48;72–96 |
| Human T-Cell RPMI 8402 | % GI | 0 | 0 | 0 | 0 | 100 |
| | Hours | 24–96 | 24–96 | 24–96 | 24–96 | 24–96 |
| Human B-Cell BALM-2 | % GI | 0;29 | 0;53;29 | 0;53 | 0;92;53 | 60;54;100 |
| | Hours | 24–72;96 | 24–48;72;96 | 24–48;72–96 | 24;48;72–96 | 24;48;72–96 |
| Human T-Cell MOLT-4 | % GI | 0 | 0 | 0 | 0 | 100 |
| | Hours | 48–96 | 48–96 | 48–96 | 48–96 | 48–96 |
| Human T-Cell HSB-2 | % GI | 0 | 0 | 0 | 0 | 100 |
| | Hours | 24–96 | 24–96 | 24–96 | 24–96 | 24–96 |
| Human T-Cell RPMI 8402 | % GI | 0 | 0 | 0 | 0 | 100 |
| | Hours | 24–96 | 24–96 | 24–96 | 24–96 | 24–96 |
| Human B-Cell SB | % GI | 0 | 0 | 0 | 0 | 100 |
| | Hours | 24–96 | 24–96 | 24–96 | 24–96 | 24–96 |
| Human B-Cell Daudi | % GI | 0 | 0 | 0;42 | 0;56;70 | 100 |
| | Hours | 24–96 | 24–96 | 24–72;96 | 24,48;72;96 | 24–96 |

| LEUKEMIA CELL TYPE | | CONCENTRATIONS PG/ML, hIFN-γ | | | | ADR, µG/ML |
|---|---|---|---|---|---|---|
| | | 0.066 | 0.66 | 2.08 | 6.66 | 0.2 |
| Human T-Cell MOLT-3 | % GI | 0 | 0 | 0 | 0 | 100 |
| | Hours | 24–96 | 24–96 | 24–96 | 24–96 | 24–96 |

NVC = No viable cells.
GI = Growth Inhibition
ADR = Adriamycin

As is apparent from the data in Tables I and II, the MOLT-3 cell line was the only T-cell line that exhibited susceptibility to both human alfa-2b interferon and human gamma interferon, whereas three B-cell lines, DND-39A, Daudi and BALM-2 exhibited sensitivity to both interferons. Since the DMD-39 A and Daudi cell lines exhibited reproducible replicative competency, they, along with the MOLT-3 cell line were selected from combination studies as being representative of susceptible T- and B-leukemia cell lines.

Combination Studies

The interferon concentrations were selected based on the data in Tables I and II. The concentrations selected for use in the combination studies were suboptimal in order to determine if they would exhibit an increased effectiveness when used in combination with each other.

Selected concentrations of human alfa-2b or human gamma interferons were added to proliferating B- or T-cell populations either simultaneously or sequentially as follows:

(a) human alfa-2b interferon at time zero followed by human gamma interferon at 24 hours;
(b) human gamma interferon at time zero followed by human alfa-2b interferon at 24 hours.

Human alfa-2b or human gamma interferons were separately added to additional individual cultures at time zero and at 24 hours. All test conditions for each cell line were run in parallel in the same experiment.

The results are defined as the survived fraction (SF) which is used to define the combination effects.

The equation for determining SF based on viable cell counts is as follows:

$$SF = \frac{NT_t - NC_o}{NC_t - NC_o}$$

$NT_t$ = Number of cells/ml from treated culture at 24, 48, 72 or 96 hours.

-continued $NC_t$ = Number of cells/ml from control culture at 24, 48, 72 or 96 hours.

$NC_o$ = Number of cells/ml from culture just prior to addition of agent.

The combination effects with regard to drug A (hIFN-α2b), Drug B (hIFN-γ) are based on the criteria presented and discussed by Valeriote et al., Cancer Chemother. Rep. 59 (Pt. 1) 895–900 (1975) and are defined as in the following equations:

1. No effect of a drug in a combination:

$SF_{A+B}=(SF_A)\times(SF_B)$ and either $SF_A$ or $SF_B=1.0$

2. Additive effect of two drugs in a combination:

$SF_{A+B}=(SF_A)\times(SF_B)$

3. Synergistic effect of two drugs in a combination:

$SF_{A+B}<(SF_A)\times(SF_B)$

4. Antagonistic effect of two drugs in a combination:

$SF_{A+B}>(SF_A)\times(SF_B)$ when $SF_A \neq SF_B \neq SF_{A+B}$

5. Subadditive effect of two drugs in a combination:

$SF_{A+B}>(SF_A)\times(SF_B)$ when $SF_A=SF_{A+B}<SF_B$ or when $SF_{A+B}=SF_A=SF_B$ 6. Interference of two drugs with each other in a combination:

$SF_{A+B}>(SF_A)\times(SF_B)$ when $SF_{A+B}=1.0$, $SF_A=1.0$, and $SF_B<1.0$ $SF_{A+B}>(SF_A)\times(SF_B)$ when $SF_{A+B}<SF_A$ but $SF_{A+B}>SF_B$ The following Table III summarizes the results of the combination treatment of leukemia cells, using recombinant human alfa-2b interferon and recombinant human gamma interferon.

TABLE III

| | | COMBINATION STUDIES WITH RECOMBINANT HUMAN ALFA-2b AND GAMMA INTERFERONS | | | |
|---|---|---|---|---|---|
| COMBINATION | LEUKEMIA CELL TYPE | COMBINATION EFFECTS | | | |
| | | 24 HR | 48 HR | 72 HR | 96 HR |
| Simultaneous Addition 0.66 μg/ml hIFN-α2b + 0.66 ng/ml hIFN-γ | Human B-Cell DND-39A | 1 | 3 | 3 | 1 |
| Sequential Addition 0.66 μg/ml hIFN-α2b at time zero + 0.66 ng/ml hIFN-γ at 24 hr | Human B-Cell DND-39A | — | 4 | 3 | 1 |
| Sequential Addition 0.66 ng/ml hIFN-γ at time zero + 0.66 μg/ml hIFN-α-2b at 24 hr | Human B-Cell DND-39A | — | 1 | 1 | 1 |
| Simultaneous Addition 0.066 ng/ml hIFN-α-2b + 6.66 μg/ml γ-IFN | Human B-Cell Daudi | 5 | 3 | 3 | 3 |
| Sequential Addition 0.066 ng/ml hIFN-α-2b at time zero + 6.66 μg/ml hIFN-γ at 24 hours | Human B-Cell Daudi | — | 4 | 1 | 1 |
| Sequential Addition 6.66 μg/ml hIFN-γ at time zero + 0.066 ng/ml hIFN-α2b | Human B-Cell Daudi | — | 1 | 4 | 1 |
| Simultaneous Addition 6.66 ng/ml hIFN-α2b + 6.66 ng/ml hIFN-γ | Human T-Cell MOLT-3 | — | 5 | 2 | 1 |
| Sequential Addition 6.66 ng/ml hIFN-α2b at time zero + 6.66 ng/ml hIFN-γ at 24 hours | Human T-Cell MOLT-3 | — | 5 | 2 | 1 |
| Sequential Addition 6.66 ng/ml hIFN-γ at time zero + 6.66 ng/ml hIFN-α2b at 24 hours | Human T-Cell MOLT-3 | — | 5 | 2 | 6 |

In Table III the combination effects are presented using the number code 1 through 6 for determining combination effects as discussed supra.

As is apparent from the data in Table III synergistic effects were found after 48 and 72 hours upon the simultaneous addition of 0.66 μg/ml of hIFN-α2b and 0.66 ng/ml of hIFN-γ against human B-cell DND-39A, and 0.066 ng/ml of hIFN-α2b and 6.66 μg/ml hIFN-γ at 48, 72 and 96 hours against human B-Cell Daudi.

Synergism was found after 72 hours upon sequential addition of 0.66 μg/ml of hIFN-α2b at time zero and 0.66 ng/ml of hIFN-γ at 24 hours.

Additive effects were found after 72 hours upon simultaneous addition of 6.66 ng/ml of hIFN-α2b and 6.66 ng/ml of hIFN-γ against Human T-Cell MOLT-3; sequential addition of 6.66 ng/ml of hIFN-α2b at time zero and 6.66 ng/ml hIFN-γ at 24 hours against Human T-Cell MOLT-3 and sequential addition of 6.66 ng/ml of hIFN-γ at time zero and 6.66 ng/ml of hIFN-α2b at 24 hours.

Although the data indicate that with the two B-cell leukemias, the most effective schedule is simultaneous addition of recombinant human alfa-2b and gamma interferons at time zero, and no synergism was observed at the concentrations and schedule for addition used in experiments with the T-cell leukemia, however, because of additive effects observed, it is expected that adjusting the concentrations and schedule might result in synergistic effects.

As is apparent from the above, each T-cell and B-cell line have different sensitivity to the combination treatment and each patient's cells must be tested to determine susceptibility to the treatment and the concentrations of the interferons used as well as the treatment regimen. Thus, the dosages of recombinant human alpha interferon and recombinant human gamma interferon when used in combination to treat susceptible leukemia cells, as well as the regimen and form of administration, are dependent on the judgment of the clinician, taking into account a variety of factors including the patient's leukemia cells response to the combination using the tests described.

Recombinant human alfa-2b interferon and recombinant human gamma interferon are each preferably administered parenterally, e.g. intravenously, intramuscularly, subcutaneously or intraperitoneally in conventional dosage forms, i.e. sterile aqueous solutions or suspensions. Pharmaceutically acceptable parenteral compositions can be prepared, for example, by diluting the interferons with sterile oxygen free water for injection to produce sterile solutions containing the appropriate concentrations of the interferons and if desired other conventional pharmaceutically acceptable suitable carriers, adjuvants, fillers, binders, disintegrants, buffers and the like.

I claim:

1. A method of inhibiting the proliferation of susceptible human lymphoma derived B cell leukemia cells which comprises treating such cells with an effective amount of a synergistic combination of recombinant human alpha interferon and recombinant human gamma interferon.

2. A method of claim 1 wherein the recombinant human alpha interferon is recombinant human alfa-2b interferon.

3. A method of claim 1 in which the alpha interferon and gamma interferon are administered sequentially.

4. A method of claim 1 in which the alpha interferon and gamma interferon are administered simultaneously.

* * * * *